United States Patent
Saeed et al.

(10) Patent No.: US 9,554,740 B2
(45) Date of Patent: Jan. 31, 2017

(54) APPARATUS FOR MEASURING AND PREDICTING PATIENTS' RESPIRATORY STABILITY

(75) Inventors: Mohammed Saeed, Cambridge, MA (US); Kwok Pun Lee, Ossining, NY (US); Colleen M. Ennett, White Plains, NY (US); Larry Eshelman, Ossining, NY (US); Larry Nielsen, Burlington, MA (US); Brian Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 602 days.

(21) Appl. No.: 12/866,067

(22) PCT Filed: Feb. 2, 2009

(86) PCT No.: PCT/IB2009/050402
§ 371 (c)(1),
(2), (4) Date: Aug. 4, 2010

(87) PCT Pub. No.: WO2009/098627
PCT Pub. Date: Aug. 13, 2009

(65) Prior Publication Data
US 2011/0029248 A1    Feb. 3, 2011

Related U.S. Application Data

(60) Provisional application No. 61/026,924, filed on Feb. 7, 2008.

(51) Int. Cl.
G06F 19/00    (2011.01)
G06Q 50/00    (2012.01)
(Continued)

(52) U.S. Cl.
CPC .......... *A61B 5/14551* (2013.01); *A61B 5/087* (2013.01); *A61B 5/7275* (2013.01);
(Continued)

(58) Field of Classification Search
CPC ......... A61B 5/0816; A61B 5/08; A61B 5/087; A61B 5/0456; A61B 5/7275; A61B 5/082; A61B 5/091
(Continued)

(56) References Cited

U.S. PATENT DOCUMENTS 6,083,173 A * 7/2000 Grant et al. .................. 600/529
6,148,814 A * 11/2000 Clemmer et al. ........ 128/200.24
(Continued)

FOREIGN PATENT DOCUMENTS

WO    9913337 A1    3/1999
WO    0245566 A2    6/2002
(Continued)

OTHER PUBLICATIONS

Ennett, C. M., et al.; Predicting Respiratory Instability in the ICU; 2008; IEEE Trans. on EMBS; pp. 2848-2851.
(Continued)

*Primary Examiner* — Alexander Satanovsky
*Assistant Examiner* — Ivan Rabovianski

(57) ABSTRACT

An apparatus (10) for predicting patient respiratory stability includes a patient data memory (24) which stores patient data for a patient (12) and an analyzer (34) in communication with the memory computes a measure of patient respiratory stability. The analyzer applies one or more rules to the patient data that are based on a plurality of parameters which in combination, have been identified as being predictive of patient respiratory instability, such as mean airway pressure (MAWP), plateau pressure (PP), arterial oxygen saturation (SaO2 or SpO2), and heart rate (HR). Based on the appli-
(Continued)

cation of the rules, the analyzer determines the measure of patient respiratory stability.

14 Claims, 3 Drawing Sheets

(51) Int. Cl.
| | |
|---|---|
| *A61B 5/145* | (2006.01) |
| *A61B 5/0205* | (2006.01) |
| *A61B 5/08* | (2006.01) |
| *A61B 5/085* | (2006.01) |
| *A61B 5/087* | (2006.01) |
| *A61M 16/00* | (2006.01) |
| *A61M 16/12* | (2006.01) |
| *A61B 5/1455* | (2006.01) |
| *A61B 5/00* | (2006.01) |
| *G06Q 50/22* | (2012.01) |

(52) U.S. Cl.
CPC ....... *A61M 16/0051* (2013.01); *G06F 19/345* (2013.01); *G06Q 50/22* (2013.01); *A61B 5/0205* (2013.01); *A61B 5/085* (2013.01); *A61B 5/0816* (2013.01); *A61M 16/12* (2013.01); *A61M 2016/0027* (2013.01); *A61M 2205/18* (2013.01); *A61M 2205/3561* (2013.01); *A61M 2205/3584* (2013.01); *A61M 2205/3592* (2013.01); *A61M 2205/502* (2013.01); *A61M 2205/52* (2013.01); *A61M 2230/06* (2013.01); *A61M 2230/205* (2013.01); *A61M 2230/42* (2013.01)

(58) Field of Classification Search
USPC ..... 702/19, 176; 128/204.18, 204.21, 204.23
See application file for complete search history.

(56) References Cited

U.S. PATENT DOCUMENTS

| | | | |
|---|---|---|---|
| 6,287,264 B1* | 9/2001 | Hoffman | 600/538 |
| 6,889,691 B2 | 5/2005 | Eklund et al. | |
| 7,425,201 B2 | 9/2008 | Euliano et al. | |
| 8,121,374 B2 | 2/2012 | Shechter | |
| 8,122,883 B2 | 2/2012 | Banner et al. | |
| 8,544,466 B2 | 10/2013 | Blanch et al. | |
| 2003/0111078 A1* | 6/2003 | Habashi | 128/204.18 |
| 2004/0118407 A1 | 6/2004 | Kandler | |
| 2005/0043644 A1* | 2/2005 | Stahmann et al. | 600/529 |
| 2007/0129647 A1 | 6/2007 | Lynn | |

FOREIGN PATENT DOCUMENTS

| | | | | |
|---|---|---|---|---|
| WO | | 2006136972 A1 | 12/2006 | |
| WO | WO 2006/136972 | * | 12/2006 | ............. A61B 5/024 |

OTHER PUBLICATIONS

Jawad, A., et al.; An Expert System for the Mechanical Ventilator Settings; 1992; pp. 1/1-1/3.

Jiang, H.; Pathological Research on Model Rat with Ventilator-induced Lung Injury; 2007; 23rd Annual Meeting of Aerospace Medicine and Aerospace Nursing; pp. 43-45.

Jin, T., et al.; Non-invasive positive pressure ventilation in treating acute respiratory distress syndrome; 2007; Journal of Clinical Pulmonary Medicine; 12(1)33-35.

Zhang, J., et al.; Clinical Research on Changes of Lung Function in Pedo-acute Lung Injury/Acute Respiratory Distress Syndrome; 2007; Practical Journal of Medicine; 23(3)321-322.

* cited by examiner

APPARATUS FOR MEASURING AND PREDICTING PATIENTS' RESPIRATORY STABILITY

CROSS REFERENCE TO RELATED APPLICATIONS

This application claims the benefit of U.S. provisional application Ser. No. 61/026,924 filed Feb. 7, 2008, which is incorporated herein by reference.

The present application relates to the field of medical assessment. It finds particular application in conjunction with the prediction of respiratory stability (or instability) using patient information and will be described with particular reference thereto. However, it is to be appreciated that the following is also applicable to prediction of other medical conditions based on patient monitoring and assessment.

Respiratory instability caused by gas exchange compromise in the lungs is a serious problem in the intensive care unit, affecting both medical and surgical patients, and is a major cause of long hospital stays and death. It is often associated with patients undergoing mechanical ventilation. It is indicated by a low PaO2/FiO2 (PF) ratio, which is the ratio of arterial oxygen partial pressure (PaO2) to fraction of inspired oxygen (FiO2). Gas exchange compromise is one aspect in the diagnosis of acute lung injury (ALI) and acute/adult respiratory distress syndrome (ARDS). ALI may be associated with a PF ratio of less than 300 and ARDS with a PF ratio of less than 200. ARDS, for example, occurs when noncardiogenic pulmonary edema (secondary to acute damage to the alveoli) leads to acute respiratory failure. ARDS has a high mortality rate of around 40-50%.

Mechanical ventilation remains the mainstay management for acute respiratory failure. A mechanical ventilator moves gas into the lungs of a patient using positive pressure to provide respiratory assistance. Although this respiratory assistance may be life saving, long-term use of a mechanical ventilator can be deleterious. Recent studies suggest that mechanical ventilation may produce, sustain, or increase the risk of lung injury resulting in gas exchange compromise. High volume stress failure is a type of stretch injury, resulting from over distension of airspaces. In contrast, shear force stress from repetitive airway closure during the tidal cycle from mechanical ventilation results in low volume lung injury.

The sooner a patient's deteriorating condition is detected, the sooner preventive action can be taken and irreparable damage potentially avoided. Several methods have been developed for mitigating lung injury, including administering medications and modifying ventilator settings. However, it has proven difficult to determine when a patient is about to suffer gas exchange compromise. Most ICU alerts are based on "rules" that use a single variable, e.g., respiration rate. These rules are subject to many false positives, i.e., false alerts, which become an annoyance and often tend to be ignored by the hospital staff or are even disabled.

The present application provides a new and improved apparatus and method for measuring and predicting patients' respiratory instability which overcomes the above-referenced problems and others.

In accordance with one aspect, an apparatus for predicting patient respiratory stability is provided. The apparatus includes a patient data memory which stores patient data for a patient and an analyzer in communication with the memory, which computes a measure of patient respiratory stability. The analyzer applies at least one rule to the patient data, the at least one rule being based on a plurality of parameters which in combination, have been identified as being predictive of patient respiratory instability. Based on the application of the rules, the analyzer determines the measure of patient respiratory stability.

In another aspect, a computer implemented method for predicting patient respiratory stability includes storing patient data for a patient and computing a measure of patient respiratory stability. The computing includes applying at least one rule to the patient data, the at least one rule being based on a plurality of parameters which in combination, have been identified as being predictive of patient respiratory stability and determining the measure of patient respiratory stability based on the applied rules.

In another aspect, a system for monitoring and predicting patient respiratory stability includes patient data memory which stores patient data for a patient and an analyzer in communication with the memory which computes a measure of patient respiratory stability. The analyzer applies a set of rules to parameters of the patient data, the set of rules having been identified as being predictive of patient respiratory stability. Based on the application of the rules, the analyzer determines the measure of patient respiratory stability. Each rule of the set of rules establishes a threshold for at least one parameter. A monitoring system for acquiring patient data related to respiratory stability supplies patient data to the memory. An output device for outputting the output measure respiratory stability to a user of the system is in communication with the analyzer.

One advantage is that a patient's respiratory instability is predicted in advance of its occurrence, allowing mitigating procedures to be administered.

Another advantage is that predictions are based on parameters which are indicative of respiratory instability such as gas exchange compromise.

Another advantage is that it reduces the likelihood of false alerts.

Another advantage is that it enables automated procedures to be initiated in order to mitigate a patient's respiratory instability.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
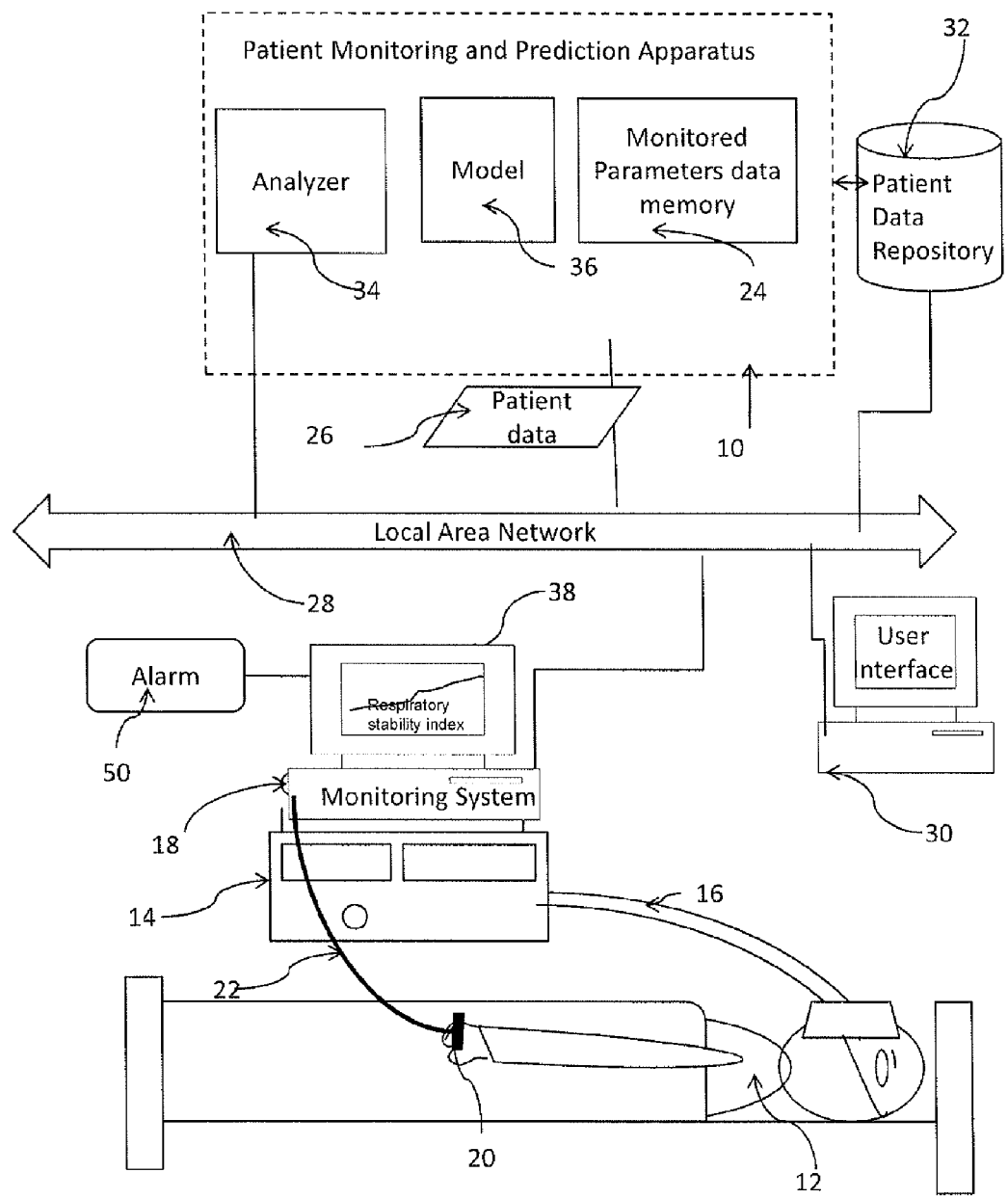
FIG. 1 is a schematic functional block diagram of one embodiment of a patient monitoring and prediction apparatus operating in a hospital environment in which a patient is undergoing mechanical ventilation.

With reference to FIG. 1, a system for monitoring and predicting patient respiratory stability (or instability) includes an apparatus 10 for predicting patient respiratory stability. The apparatus 10 provides a measure of the stability of a patient's respiratory system based on clinical data for the patient. The exemplary apparatus 10 provides an instantaneous, ongoing measure of the stability of a patient's respiratory system, e.g., the likelihood that the patient will be subject to gas exchange compromise, and perhaps develop acute/adult respiratory distress syndrome (ARDS)

or acute lung injury (ALI). The measure can be used as the basis for predictive alerts that indicate which patients are likely to develop serious respiratory problems if preventive action is not taken. An alert can be issued when the measure of respiratory stability indicates that the patient will soon become unstable. It should be noted that while patient respiratory instability is defined in the exemplary embodiment as a condition which is associated with a PF ratio of less than 300 (and thus respiratory stability is considered to be associated with a PF ratio of 300 or higher), it is to be appreciated that the threshold of respiratory instability could be defined in other terms, such as a PF ratio of less than 320 or a PF ratio of less than 250. Other measures for defining respiratory instability which are similarly based on arterial oxygen pressures or the like are also contemplated.

In one embodiment, the apparatus 10 analyzes clinical data over a period of time to determine the likelihood that a patient 12 will suffer from respiratory instability. In particular, the apparatus 10 monitors a set of patient parameters derived from the clinical data which have been shown to be linked to respiratory instability. The apparatus 10 applies rules for classifying patients based on the parameter values. By basing the measurement of respiratory stability upon a combination of multiple features (e.g., arterial oxygen saturation, heart rate, mean airway pressure, plateau pressure) a higher degree of specificity (i.e., fewer false alerts) can often be achieved while maintaining a useful degree of sensitivity (i.e., true alerts).

The exemplary apparatus 10 is suitable for use in hospitals, other health care facilities such as home care facilities, nursing homes, and the like for a variety of health care applications.

In the exemplary embodiment, a mechanical ventilator 14 supplies gas to the patient's lungs at a pressure higher than atmospheric pressure via an air supply tube 16. The gas is generally air, optionally enriched with oxygen. An associated monitoring system 18 monitors the patient parameters, e.g., by acquiring patient data related to respiratory stability from which the parameters can be computed. Exemplary patient parameters may include parameters selected from:

Mean airway pressure (MAWP), e.g., expressed in mm Hg,

Plateau pressure (PP), e.g., expressed in mm Hg,

Peak inspiration pressure (PIP), e.g., expressed in mm Hg,

Dynamic lung/chest compliance ($C_{dyn}$), e.g., expressed in mL/cm $H_2O$,

Static respiratory compliance ($C_{stat}$), e.g., expressed in mL/cm $H_2O$,

Respiratory rate (RR), e.g., expressed in breaths/min,

An oxygen saturation measure, such as saturation of peripheral oxygen (SpO2), e.g., expressed in % oxygenation, and/or saturation of oxygen in arterial blood flow (SaO2), Heart rate (HR), e.g., expressed in beats/min, White Blood Cell Count (WBC), and Net Fluid Balance.

In general, the parameters are based on physiological data acquired from the patient, although some parameters may be based, at least in part, on mechanical settings, such as ventilator settings. For example SaO2 is the percentage of oxygen saturation in arterial blood, i.e., a measurement of the amount of oxygen attached to the haemoglobin cell in the circulatory system. For normal patients, SaO2 is around 96%. SaO2 is generally measured by pulse oximetry and is then referred to as SpO2. Dynamic lung/chest compliance is calculated using observed tidal volume (Vt in mL), PIP and positive end expiratory pressure (PEEP in mmHg). Static respiratory compliance is calculated using Vt, PP and PEEP. White Blood Cell Count (WBC) is the number of leucocytes (white blood cells)/cubic millimeter of blood. Normal is between 5,000 and 9,000. If greater than 10,000, the patient has Leucocytosis; if less than 5,000, the patient has leucopenia. WBC is usually expressed as a number between 1 (1,000) and 16 (16,000). Net Fluid Balance is the total fluid intake−total fluid output=0 under normal circumstances. It is typically measured in ml/day.

In a typical hospital environment, MAWP, PP, PIP, and Vt are all measured values that are typically recorded approximately every four hours for patients on mechanical ventilation. PEEP is a setting on a mechanical ventilator that is selected by the respiratory therapist or other appropriate caregiver. RR, SpO2, and HR are usually monitored on a continuous basis. For example, SpO2 may be measured by an $SpO_2$ fingertip probe 20 which may be connected monitoring system 18 by a cable 22 or by a wireless connection. Heart rate can be measured by the fingertip probe 20, EKG electrodes, or the like. Respiratory rate can be measured via the ventilator 14.

It is to be appreciated that the apparatus 10 is also suited to use with patients who are not undergoing mechanical ventilation.

The apparatus 10 includes a monitored parameters data memory 24 which stores the parameter values and/or acquired patient data from which the parameter values are determined. The acquired data/parameter values are associated with the particular patient in memory 24, e.g., by a patient ID number. Acquired patient data 26 may be communicated from the monitoring system 18 to the memory 24 automatically, e.g., over a network 28 such as a wired or wireless local area network or a wide area network, such as the Internet. Alternatively, some (e.g. Net Fluid Balance) or all of the patient data may be manually input to data memory 24, either directly or indirectly, e.g., by a healthcare professional, based on measurements made, e.g., using a user interface 30, such as a workstation, or input from a data storage device, such as an optical disk, hard drive, usb device, memory card, or the like. Additionally, other patient data (e.g. laboratory data, such as WBC) may automatically be input to data memory 24, via the network 28. In another embodiment, all acquired patient data is stored in a hospital-wide or other medical system-wide patient data repository 32, which is accessible to the apparatus 10, e.g., via the network.

The apparatus 10 includes an analyzer 34, which, for a predetermined time window, provides a measure of the stability of a particular patient's respiratory system based on monitored clinical data for the patient stored in data memory 24. The time window may be, for example, the next two hours, twelve hours, or twenty-four hours, or a time period which begins in the future, such as one which starts in two, twelve, or twenty-four hours. In particular, the analyzer applies a set of rules to the patient data which together are predictive of respiratory instability (e.g., a likelihood that respiratory instability will follow). These rules may be stored in a model 36. The rules may run continuously (e.g., for monitored data), or upon manual entry of new data or validated vitals (e.g., in the case of net fluid balance), or upon new data becoming available (e.g., WBC from the laboratory tests).

The exemplary apparatus 10 may be implemented in a computing device such as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, or PAL, or the like. Analyzer 34 may be in the form of software, hardware, or a combination thereof. In one embodiment the analyzer 34 comprises software instructions stored in memory which are executed by an associated processor of the computing device. The patient data memory 24 which may be the memory that stores the analyzer or a separate memory, may represent any type of computer readable medium such as random access memory (RAM), read only memory (ROM), magnetic disk or tape, optical disk, flash memory, or holographic memory. In one embodiment, the memory 24 comprises a combination of random access memory and read only memory.

Figure 2:
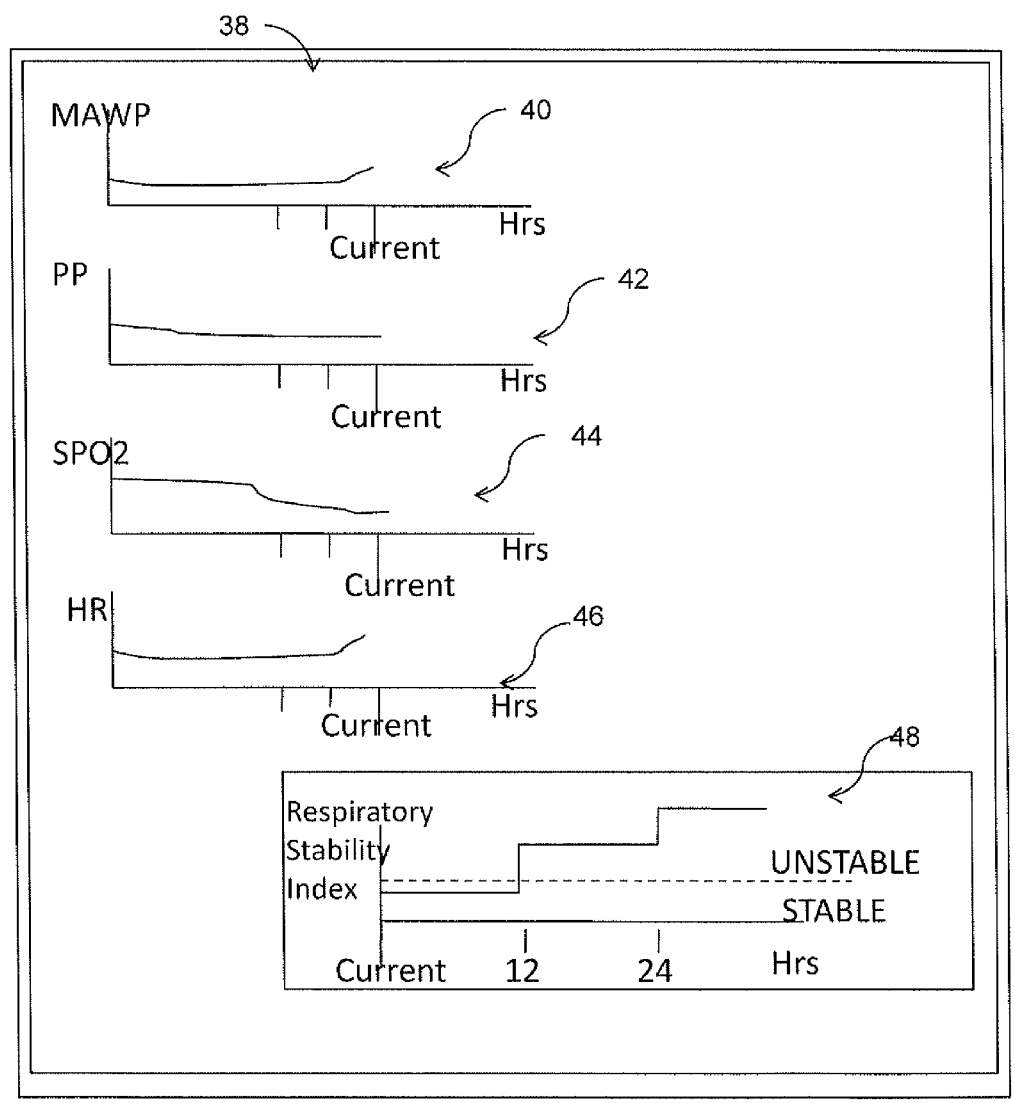
FIG. 2 illustrates a vital signs display on which respiratory stability measure is displayed.

The determined respiratory stability measure may be output from the apparatus 10 e.g., to the patient record repository 32 or to an output device, such as a vital signs display monitor 38, printer, alarm system, or the like, via the local area network 28. The monitor 38 may be local to the patient, e.g., a bedside monitor, or may be located in a vital signs monitoring station or surveillance center. Indeed, once the collected data is sent to and stored in the patient record repository 32, it can be used by any device on the network 28 which has the proper authorization to access it. For example, as shown in FIG. 2, the monitor 38 may display each of a set of measured parameters 40, 42, 44, 46, as well as the predictive measure 48 (shown as a respiratory stability index) of the stability/instability of the patient's respiratory system for one or more time windows, here 12 and 24 hrs. Optionally, an alarm 50, linked to the monitor 38, is actuated if the measure indicates instability.

Figure 3:
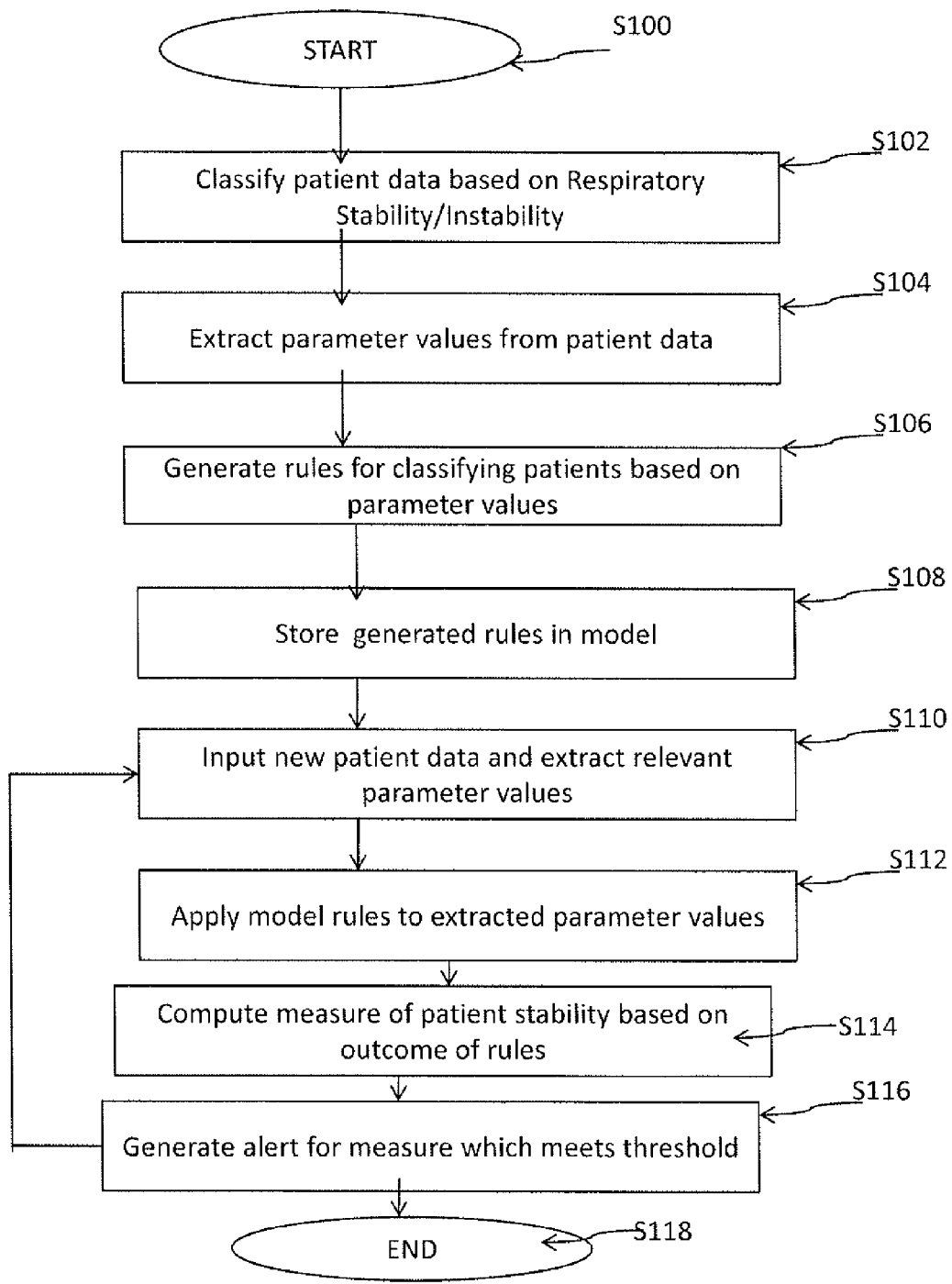
FIG. 3 is a flowchart illustrating a method for measuring and predicting patients' respiratory stability in accordance with another embodiment.

FIG. 3 illustrates an exemplary method for measuring and predicting patients' respiratory stability. The method begins at S100.

At S102, a corpus of prior patient data is collected and classified according to whether not the patient suffered respiratory instability.

At S104, parameter values are extracted from the patient data.

At S106, rules are identified, based on parameters whose values extracted from the patient data have some ability to distinguish between the (two) groups. The set of rules can therefore be considered to be predictive of patient instability (or stability) for new patients which are not yet in a state of respiratory instability.

At S108, the rules are stored in the model 36.

At S110, new patient data is input and parameter values extracted.

At S112, a set of the stored rules is applied to the extracted patient parameter values. The rules may be selected based on a selected time window.

At S114, a measure of patient stability is computed, based on the outcome of the applied rules and output in the form of data.

At S116, for a patient whose stability measure meets or exceeds a predetermined threshold indicative of instability, an alert may be provided to medical personnel, so that appropriate treatment can be provided.

Steps S110-S116 may be repeated for the same patient at intervals, such as at least once every four hours or on a semi-continuous basis, e.g., each time new patient data is input. The method ends at S118. Further details of the method will now be provided.

The model 36 can be built (S102-S108) by applying machine learning algorithms to a large corpus of prior patient data comprising data for cases in which respiratory instability was subsequently observed (within the prediction time window, e.g., 2, 12, or 24 hrs) and cases in which it was not (i.e., the patient was considered to be stable). In one embodiment, retrospective data from ICU patients is used to develop two reference data sets: a set of unstable patients who developed serious respiratory problems and a set of patients who did not develop such problems. In another embodiment, retrospective data from ICU patients is annotated by a health care provider or other trained personnel based on medical records to indicate which patients developed serious respiratory problems and which did not.

The machine learning techniques identify, from the corpus, which parameters are most associated with onset of respiratory instability and rules, based on these parameters, which are predictive of onset of respiratory instability. In general a set of one or more rules is developed which employs at least two of the parameters as variables. In generating the rules, thresholds may be set for the parameters. As will be appreciated, some of the thresholds may require the parameter value(s) to be at or below the threshold (e.g., in the case of SpO2) for the rule to be satisfied and the patient classified as unstable, while others may require the parameter value to be at or above the threshold (e.g., in the case of MAWP, PP, or HR) for the rule to be met.

For example, one type of rule may include only a first of the parameters and specify a relatively challenging threshold value for that parameter for which the rule is satisfied and the patient is predicted to be unstable, e.g., within the specified time window. Another type of rule may include at least two parameters (one of which may be the first parameter). For this type of rule, threshold values for each of the parameters must be met for the rule to be met, e.g., the patient to be considered unstable. Generally, where one of these parameters is the first parameter, its threshold may be less challenging than for the first type of rule when it is the sole parameter. For example, MAWP may be required to be above 17 in the first type of rule and above 12.6 in the second type of rule. Other rules are also contemplated in which a relationship between parameters (such as a ratio) must meet a threshold for the rule to be satisfied.

In one embodiment, at least one of the rules from the set of rules must be satisfied for the patient to be determined to be unstable (or stable). In other embodiments, more than one rule must be satisfied. In some embodiments, rather than a binary measure (stable/unstable) the measure of patient stability may be a continuously variable index. In this embodiment, one or more of the rules may be taken into account. Alternatively the rule or rules may be a weighted function of two or more parameters, where the weights take into account relative importance of the parameters.

Additionally or alternatively, the measure of patient stability may be based on two or more sets of parameter values which are acquired at different times. For example, one or more of the rules may be met by a threshold change in one or more parameter values over a predetermined time period.

The rules may vary, dependent on the prediction time window and thus the model 36 may have different sets of rules for each of a plurality of time windows. For example, the thresholds may be different, depending on the time window. Additionally, the rules may vary by patient type, e.g., mechanically ventilated vs., no mechanical ventilation, or according to age, sex, medical condition, or other factors. Accordingly, each of these factors may be used in generating different sets of rules applicable to that class of patients.

For example, in one instantiation, patients, all of whom were on ventilators, were divided into two sets based on whether the patients were subject to respiratory instability, as indicated by a low (e.g., <300) PF ratio for a sustained period. Machine learning techniques are used to discover rules that will correctly classify the patients from the two data sets using the identified variables. It was found that certain measured parameters tended to differentiate among these two sets: mean airway pressure (MAWP in mmHg), plateau pressure (PP in mmHg), peak inspiration pressure (PIP in mmHg), dynamic lung/chest compliance ($C_{dyn}$ in mL/cmH2O), static respiratory compliance ($C_{stat}$), respiratory rate (RR in breaths/min), saturation of peripheral oxygen as measured by pulse oximetry (SpO2 in % oxygenation), and heart rate (HR in beats/min). Using these parameters, machine learning techniques were used to develop algorithms for classifying patients as either unstable or stable with regard to gas exchange compromise. Below is an example of one of the rule sets discovered:

MAWP>17→unstable

MAWP>12.6 and SpO2<=97 and HR>86.5→unstable

PP>23.8 and HR>90.5 and SpO2<=97.5→unstable

Otherwise→stable

In this example, there are three rules for identifying respiratory unstable patients and a fourth, default stable rule. Note that in this example, although data for eight features (candidate parameters) were provided to the machine learning algorithms, this rule set only uses four of them. The other features on the list were found not to be as useful for this set of patients. As will be appreciated, the parameters are not limited to those listed above. For example, two or three of these parameters may be used alone or in combination with other parameters. Besides variables based on ventilator readings or monitoring data, other possible variables might be based on lab data (WBC), manual entry (Net Fluid Balance), radiological imagery (for volume estimation) and surgical history. Also, as previously noted, while the above example of a classification algorithm is in the form of a set of rules, these rules can be transformed into a single continuous index (rather than a binary alert) by transforming the binary thresholds into continuous functions varying from 0 to 1 and combining these continuous functions using the standard fuzzy logic operators.

The exemplary embodiment is suitable for the use in the ICU for providing predictive alerts for gas exchange compromise patients. However, it could be applied in other ways. Alerts could be developed for subsets of problems within the gas exchange compromise category, e.g., ALI and ARDS. In other embodiments, the methods described herein may be applied to develop a respiratory component of an overall patient acuity measure. Or the approach could be applied to using high resolution data whether in the ICU or outside the ICU.

In one embodiment, the data provided by the monitoring system 10 is analyzed to retrospectively determine how the medical personnel reacted to certain measures and how the interventions affected the patient outcome. The administrator can evaluate how well the medical personnel managed respiratory instability of the patient, and modify the rules or time window accordingly.

The method illustrated in FIG. 3 may be implemented in a computer program product that may be executed on a computer. The computer program product may be a tangible computer-readable recording medium on which a control program is recorded, such as a disk, hard drive, or may be a transmittable carrier wave in which the control program is embodied as a data signal. Common forms of computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, transmission media, such as acoustic or light waves, such as those generated during radio wave and infrared data communications, and the like, or any other medium from which a computer can read and use.

The exemplary method may be implemented on one or more general purpose computers, special purpose computer (s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, or PAL, or the like. In general, any device, capable of implementing a finite state machine that is in turn capable of implementing the flowchart shown in FIG. 3, can be used to implement the method for predicting respiratory stability.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. An apparatus for predicting onset of patient respiratory instability wherein patient respiratory instability is defined as a condition associated with a low ratio of arterial oxygen partial pressure ($PaO_2$) to fraction of inspired oxygen ($FiO_2$), the apparatus comprising:

a vital signs display monitor configured to acquire and display patient data of a patient related to respiratory stability including at least Mean Airway Pressure (MAWP) and Plateau Pressure (PP) parameters; and an analyzer comprising a microprocessor or microcontroller, the analyzer programmed to compute at least one measure of predicted patient respiratory stability over a prediction time interval of duration 36 hours or less and having a starting time in a range of a current time to 24 hours in the future, the analyzer applying at least one rule to the patient data, the at least one rule being based on a plurality of parameters including at least one of the MAWP and PP parameters monitored by the monitoring system which, in combination, have been identified as being predictive of patient respiratory instability, and based on the application of the at least one rule, determines the measure of predicted patient respiratory stability over the prediction time interval, the analyzer further configured to output an alert when the measure of predicted patient respiratory stability over the prediction time interval meets a threshold indicative of respiratory instability;

wherein the vital signs display monitor is further configured to display the measure of predicted patient respiratory stability over the prediction time interval computed by the analyzer.

2. The apparatus of claim 1, further comprising a model in communication with the analyzer which stores the at least one rule.

3. The apparatus of claim 1, wherein the plurality of parameters further include at least two of the group consisting of:

an oxygen saturation measure (SpO2 or SaO2);
Heart rate (HR);
Peak inspiration pressure (PIP);
Dynamic lung/chest compliance ($C_{dyn}$);
Static respiratory compliance ($C_{stat}$);
Respiratory rate (RR);
White Blood Cell Count (WBC); and
Net Fluid Balance.

4. The apparatus of claim 3, wherein the plurality of parameters include the group consisting of:
Mean airway pressure (MAWP);
Plateau pressure (PP);
Saturation of peripheral oxygen (SpO2); and
Heart rate (HR).

5. The apparatus of claim 4, wherein the at least one rule comprises:
(1) if MAWP>17 mmHg then patient respiration is unstable;
(2) if MAWP>12.6 mmHg and SpO2<=97% and HR>86.5 beats per minute then patient respiration is unstable;
(3) if PP>23.8 mmHg and HR>90.5 beats per minute and SpO2<=97.5% then patient respiration is unstable; and
(4) if rules (1), (2), and (3) are not met, then patient respiration is stable.

6. The apparatus of claim 1, wherein the at least one rule comprises a set of rules, each rule specifying a threshold for at least one of the parameters which must be met for the rule to be satisfied to determine the measure of predicted patient respiratory stability over the prediction time interval.

7. The apparatus of claim 6, wherein the set of rules includes a first rule which specifies a threshold for a first of the parameters and a second rule which specifies a threshold for a second of the parameters.

8. The apparatus of claim 7, wherein the second rule specifies a different threshold for the first parameter from the first rule.

9. The apparatus of claim 1, wherein the measure of predicted patient respiratory stability over the prediction time interval is a binary measure.

10. The apparatus of claim 1, wherein the measure of predicted patient respiratory stability over the prediction time interval is a variable value.

11. The apparatus of claim 1, wherein the at least one rule applied by the analyzer is dependent on the prediction time interval.

12. A method for predicting onset of patient respiratory instability caused by gas exchange compromise in the lungs, the method comprising:
monitoring a plurality of parameters related to respiratory stability including at least Mean Airway Pressure (MAWP) and Plateau Pressure (PP) by acquiring patient data for a patient and displaying the acquired patient data on a vital signs display monitor;
computing a measure of patient respiratory stability over a prediction time interval of duration 36 hours or less and having a starting time in a range of a current time to 24 hours in the future by operations performed by a microprocessor or microcontroller including (i) applying at least one rule to the patient data, the at least one rule operating on the monitored plurality of parameters including at least one of the MAWP and PP parameters, (ii) determining the measure of patient respiratory stability based on the applied at least one rule, and (iii) applying a threshold to the measure of patient respiratory stability to generate a prediction regarding onset of patient respiratory instability; and
displaying the computed measure on the vital signs display monitor.

13. The method of claim 12, further comprising:
acquiring a corpus of patient data of prior patient data comprising data for cases in which respiratory instability was subsequently observed for a set of patients;
classifying patients according to whether the patients exhibited respiratory instability; and
generating the at least one rule based on the acquired corpus and patient classifications.

14. The method of claim 13, wherein the measure of predicted patient respiratory stability is computed over a prediction time interval of duration 36 hours or less and having a starting time in a range of a current time to 24 hours in the future and wherein the prediction time interval includes a first selectable time interval and a second selectable time interval, the method further comprising:
generating a first set of rules of the at least one rule applicable to a first selectable time interval; and
generating a second set of rules of the at least one rule applicable to a second selectable time interval.

* * * * *